United States Patent
Auger et al.

[11] 3,951,875
[45] Apr. 20, 1976

[54] PERFUME COMPOSITIONS

[76] Inventors: Bernard Auger, Residence les Marronniers, Grasse; Pierre Pesnelle, 1 rue de Cannes, Le Cannet; Paul José Teisseire, 14 Avenue Pierre Semard, Grasse, all of France

[22] Filed: Dec. 20, 1974

[21] Appl. No.: 534,737

Related U.S. Application Data

[62] Division of Ser. No. 328,928, Feb. 2, 1973, Pat. No. 3,901,924.

[30] Foreign Application Priority Data

Feb. 16, 1972 France .............................. 72.05139

[52] U.S. Cl. .............................. 252/522; 260/345.2
[51] Int. Cl.² ..................... A61K 2/46; C11B 9/00
[58] Field of Search ................................. 252/522

[56] References Cited
UNITED STATES PATENTS

3,796,727   3/1974   DeBoer .......................... 260/345.2

Primary Examiner—Herbert Levine
Assistant Examiner—G. E. Schmitkons
Attorney, Agent, or Firm—Wallenstein, Spangenberg, Hattis & Strampel

[57] ABSTRACT

Oderiferous compositions containing certain novel 1,1-dialkyl naphthopyrans are disclosed. The 1,1-dialkyl naphthopyrans involved have the formula

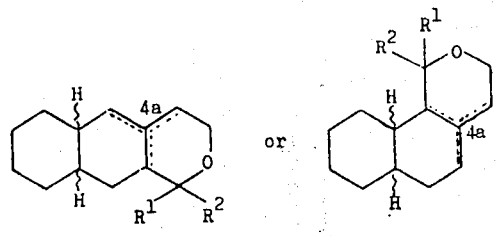

wherein $R^1$ and $R^2$ each represent a lower alkyl group having from 1 to 4 carbon atoms and the dotted lines indicate an optional double bond emanating from the carbon atom in the 4a position, and mixtures thereof. $R^1$ and $R^2$ preferably both represent methyl.

Processess for the production of said 1,1-dialkyl naphthopyrans are also disclosed.

12 Claims, No Drawings

PERFUME COMPOSITIONS

RELATED APPLICATIONS

This is a division of application Ser. No. 328,928, filed Feb. 2, 1973 now U.S. Pat. No. 3,901,924.

DETAILED DESCRIPTION OF THE INVENTION

The present invention relates to perfumes and odoriferous products containing certain naphthopyrans.

According to the present invention there are provided perfumes and odoriferous products containing naphthopyrans having the general formula:

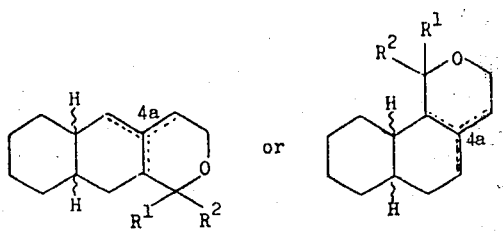

I wherein $R^1$ and $R^2$ each represent a lower alkyl group having from 1 to 4 carbon atoms and the dotted lines indicate an optional double bond emanating from the carbon atom in the 4a position, and mixtures thereof. $R^1$ and $R^2$ preferably both represent methyl.

The naphthopyrans utilized according to the invention may be prepared by condensing 2-hydroxyethyl-2-hydroxy-decalin having the formula:

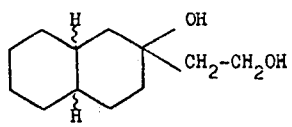

II with a di-lower alkyl ketone having the formula:

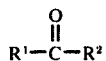

III wherein $R^1$ and $R^2$ have the meanings given above, and then if desired, subjecting the product to catalytic hydrogenation.

The ketone of formula III is preferably acetone, but other ketones such as methylethyl ketone, methylisobutyl ketone, ethylisobutyl ketone, methyl-n-propyl ketone or diethyl ketone may also be used.

The condensation is conveniently effected in a conventional manner using an acid catalyst. Examples of suitable acid catalysts include sulphuric acid, perchloric acid, p-toluenesulphonic acid and boron trifluoride etherate.

The condensation gives rise to a mixture of the isomers having the following formulae:

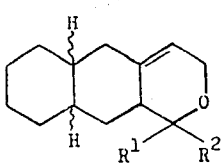

IV

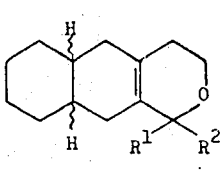

V

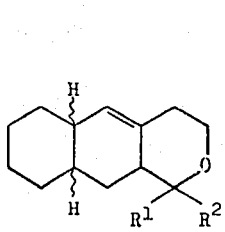

VI

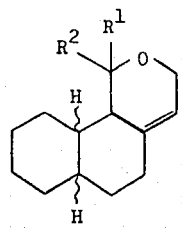

VII

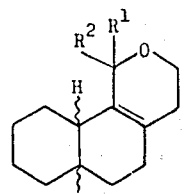

VIII

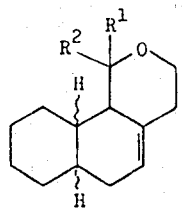

IX wherein $R^1$ and $R^2$ have the meanings given above.

Under the reaction conditions employed herein, the compounds having the formulae IV and VII are formed in the largest yields and the compounds having the formulae V and VIII only in a small proportion. The individual isomers of the mixture of isomers can be separated from each other and isolated in pure form by conventional processes such as for example by chromatography.

The starting material of formula II may conveniently be prepared by reducing a corresponding ester having the formula:

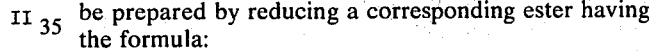

X wherein R represents an alkyl group having from 1 to 6 carbon atoms. The reduction may conveniently be effected by conventional methods for example by treatment with sodium in a suitable solvent such as anhydrous ethanol or with diisobutyl aluminium hydride.

The catalytic hydrogenation of the mixture of the isomers IV to IX to obtain the saturated compounds of formulae:

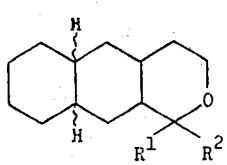 and 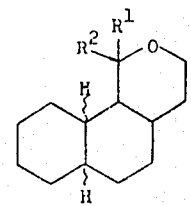

XI　　　　　　XII may be effected by conventional methods such as for example using platinum or palladium on carbon or Raney nickel, as the catalyst.

The starting material having the formula X may conveniently be prepared by treating a mixture of cis and trans β-decalones with an α-halo ester having the formula: X—CH$_2$COOR wherein X represents a halogen atom, preferably bromine, and R represents an alkyl group having from 1 to 6 carbon atoms, in the presence of zinc. The progress of the reaction can be assisted by addition of a small quantity of activator for the zinc. Examples of suitable activators include iodine, mercuric chloride, mercuric bromide and copper. The group R is preferably methyl or ethyl.

The compounds of formula I have remarkable odors which are in general reminiscent of the odor of ambergris. They are hence useful in the preparation of odoriferous compositions. They may be used in the preparation of perfumes as well as for perfuming commercial products such as toilet waters, cosmetics, soaps, washing liquids and other products. The quantity in which the compounds according to the invention may be used varies widely, depending on the nature of the product and the desired odour intensity. In the preparation of concentrates, the naphthopyrans may for example conveniently be used in a proportion of from 1 to 15% by weight. For the preparation of perfumes of the floral type the compounds may be used in a proportion of 1 to 5% by weight, and for perfumes of the "chypre" type in a proportion of from 5 to 10% by weight. A proportion of from 5 to 10% by weight is also an appropriate proportion for the preparation of concentrates utilisable for perfuming soaps. In certain applications concentrations of 1 to 5% by weight of the compounds of formula I, may be used.

The invention will now be illustrated with reference the following Examples.

EXAMPLE 1

94 g Of 2-hydroxyethyl-2-hydroxy-decalin are dissolved in 1500 ml of acetone; 30 ml of concentrated sulphuric acid are added thereto and the solution is left for seven hours at ambient temperature. The solution is then neutralised with 1000 ml of a 9% aqueous solution of sodium bicarbonate, extracted with benzene and washed to neutrality thereby giving 70 g of crude product which are rectified. There are thus obtained 45 g of a mixture of decahydro-1,1-dimethyl-1H-naphtho-[2,3-c]pyrans and decahydro-1,1-dimethyl-1H-naphtho [1,2-c]pyrans having the formulae IV to IX given above. This represents a yield of about 40%. The product has b.p.$_{1.0}$ = 88°–90°C and $n_D^{20}$ = 1.5110.

The starting material may be prepared as follows:

a. To 112 g of powdered electrolytic zinc which is covered by benzene and to which has been added some crystals of mercuric chloride there is added dropwise several ml of a solution composed of the following mixture: 228 g of β-decalone, 228 g of ethyl bromoacetate and 450 ml of anhydrous benzene. The mixture is then refluxed to initiate the reaction; once the reaction has started heating is stopped and the rest of the solution is added so as to maintain reflux. After the addition is completed, refluxing is continued for a further two hours. After cooling, the mass is hydrolysed with 850 ml of a 10% aqueous solution of sulphuric acid. The mass is then extracted with benzene, the benzene solutions washed to neutrality, the benzene distilled and 330 g of crude product are obtained which are rectified under 0.5 mm and which yields 310 g of pure 2-carbethoxy-methyl-2-hydroxy-decalin. Yield = 86%, b.p.$_{0.5}$ = 112°–115°C; $n_D^{15}$ = 1.4863.

b$_1$. 86.25 g Of small pieces of sodium are added to 60 g of 2-carbethoxy-methyl-2-hydroxy-decalin and 900 ml of anhydrous ethyl alcohol. A vigorous reaction sets in which causes the reaction medium to reflux. Reflux is maintained for 1 hour. The mass is cooled, 1000 ml of water added, the alcohol distilled off and the residue is taken up in a little warm water. After cooling the mass is extracted three times with 250 ml of diethyl ether. The ethereal solutions are washed to neutrality and distilled; there are thus obtained 40 g of crude product which are rectified under 0.5 mm. This rectification gives 22 g of 2-hydroxyethyl-2-hydroxy-decalin (b.p.$_{0.5}$ = 138°–140°C), which represents a conversion of about 42%.

b$_2$. A solution of 235 g of diisobutyl aluminium hydride in 300 ml of anhydrous benzene is added dropwise to a mixture of 120 g of 2-carbethoxymethyl-2-hydroxy-decalin and 120 ml of anhydrous benzene under nitrogen. During the addition the temperature of the reaction mass is held between 15° and 20°C. This temperature is maintained for a further two hours after the end of the addition. The mass is then cooled to 0°C and hydrolysed with 1500 ml of a 10% aqueous solution of sulphuric acid. The temperature is allowed to return to ambient, the organic layer decanted and the mother liquor extracted twice with 250 ml of benzene. The benzene extracts are then combined and washed to neutrality. After distillation of the solvent on a water bath under reduced pressure the crude product is rectified giving 72 g of 2-hydroxyethyl-2-hydroxy-decalin (72% yield) having b.p.$_1$ = 147°.

EXAMPLE 2

110 g Of decahydrodimethylnaphthopyran prepared as described in Example 1, is introduced into a 250 ml autoclave followed by 50 ml of absolute ethyl alcohol and 3.3 g of 5% palladium on carbon. Hydrogen is then introduced under a pressure of 80 kg/cm². After eight hours at 120°C the hydrogenation is stopped. After cooling and filtration of the catalyst the alcohol is distilled off under reduced pressure and 100 g of crude product are obtained which are rectified. There are thus obtained 90 g of a product (80% yield) having the following constants: b.p.$_{0.5}$ = 95°–96°C; $n_D^{15}$ = 1.5010 and being a mixture of perhydro-1,1-dimethyl-naphtho[2,3-c]-pyran and perhydro-1,1-dimethyl-naphtho[1,2-c]-pyran.

The use of the compound in accordance with the present invention as odoriferous agents is illustrated in the following Examples A to E.

| Example A | Concentrate for perfume |
|---|---|
| 40 | Ylang Extra oil |
| 120 | Bergamet Peel oil Extra |
| 50 | Benzyl acetate |
| 80 | Phenylethyl alcohol |
| 220 | Methylionone |
| 20 | Florentine iris absolute |
| 20 | Galbanum oil |
| 20 | Phenylacetic aldehyde, 50% in ethyl phthalate |
| 20 | C.11 aldehyde (100%), 10% in ethyl phthalate |
| 20 | Rose of May absolute |
| 80 | Jasmin absolute |
| 70 | Benzyl salicylate |
| 60 | Dioxa-2,7-cycloheptadecanone, 50% in ethyl phthalate |
| 80 | Vetiveryl acetate |
| 100 | Mixture of the isomers of the aforesaid formulae IV to IX |
| 1000 | |

| | Example B Concentrate for perfume (Chypre type) |
|---|---|
| 10 | Benzyl acetate |
| 20 | Artemisia oil |
| 30 | Bergamot Zest Peel oil Extra |
| 35 | Lemon Peel oil Extra |
| 40 | Linalol |
| 50 | Lavender oil Laragne 50% |
| 15 | Neroli oil |
| 40 | Ylang Ylang oil Nossi Be |
| 20 | Rose of May absolute |
| 20 | C.19 aldehyde (100%), 10% in ethyl phthalate |
| 30 | C.11 aldehyde (100%), 10% in ethyl phthalate |
| 50 | α-Amylcinnamicaldehyde |
| 20 | Coriander oil |
| 2 | Galbanum oil |
| 10 | Geranium Bourbon oil |
| 20 | Geraniol |
| 100 | Hydroxycitronnellal |
| 100 | Jasmin absolute |
| 10 | Oak Moss absolute |
| 30 | Forest moss absolute |
| 30 | Sandalwood oil East Indies |
| 20 | Methylionone |
| 20 | Patchouli oil Grasse |
| 8 | Isobutylquinoline |
| 10 | Amyl salicylate |
| 20 | Benzyl salicylate |
| 10 | Styrax oil |
| 20 | Vetiver oil Bourbon |
| 20 | Coumarin |
| 30 | Dioxa-2,7-cycloheptadecanone, 50% in ethyl phthalate |
| 10 | C.16 aldehyde (100%), 10% in ethyl phthalate |
| 60 | Musk Ambrette |
| 20 | Musk ketone |
| 70 | Mixture of the isomers of the aforesaid formulae IV to IX |
| 1000 | |

| | Example C Toilet water |
|---|---|
| 180 | Bergamot Peel oil Extra |
| 260 | Lemon Peel oil Extra |
| 20 | Bornyl acetate |
| 30 | Scotch Pine oil |
| 40 | Linalol |
| 20 | Geranium Bourbon oil |
| 100 | Lavender oil Laragne |
| 20 | Artemisia oil |
| 120 | Hydroxycitronellal |
| 20 | Methylionone |
| 10 | Eugenol Extra |
| 60 | Benzyl salicylate |
| 60 | Sage Clary oil Grasse |
| 20 | Musk ketone |
| 40 | Mixture of the isomers of the aforesaid formulae IV to IX |
| 1000 | |

| | Example D Perfume (Chypre) |
|---|---|
| 50 | Benzyl acetate |
| 50 | Linalyl acetate |
| 100 | Lemon Peel oil Extra |
| 20 | Coriander oil |
| 5 | Neroli oil |
| 50 | Ylang Ylang oil extra |
| 20 | C.11 aldehyde, 10% in ethyl phthalate |
| 20 | C.12 aldehyde, 5% in ethyl phthalate |
| 80 | α-Hexylcinnamicaldehyde |
| 80 | Jasmin absolute |
| 50 | Rose of May absolute |
| 20 | Citronellol |
| 60 | Hydroxycitronellal |
| 40 | Rose of the Orient oil |
| 10 | Styrallyl acetate |
| 80 | Caryophyllenyl acetate |
| 30 | Forest moss absolute |
| 15 | Coumarin |
| 80 | γ-Methylionone |
| 10 | Patchouli oil |
| 20 | Civet absolute, 10% in ethyl phthalate |
| 20 | Benzoin resinoid |
| 40 | Dioxa-2,7-cycloheptadecanone |
| 50 | Mixture of perhydro-1,1-dimethyl-naphtho[2,3-c]pyran and perhydro-1,1-dimethyl-naphtho[1,2-c]pyran |
| 1000 | |

| | Example E Perfume (Fougere) |
|---|---|
| 30 | Petitgrain oil Grass |
| 30 | Linalol |
| 170 | Bergamot Peel oil Extra |
| 280 | Lemin Peel oil Extra |
| 40 | Sage Clary Grasse |
| 20 | Geranium Bourbon oil |
| 20 | C.12 aldehyde, 5% in ethyl phthalate |
| 40 | Forest moss absolute |
| 10 | Vetiver Bourbon oil |
| 100 | Hydroxycitronellal |
| 40 | Sandalwood oil |
| 30 | γ-Methylionone |
| 20 | Dioxa-2,7-cycloheptadecanone |
| 70 | Linalyl acetate |
| 100 | Mixture of perhydro-1,1-dimethyl-naphtho[2,3-]pyran and perhydro-1,1-dimethyl-naphtho[1,2-c]pyran, 50% in ethyl phthalate |
| 1000 | |

We claim:

1. An odoriferous composition containing naphthopyran of the formula

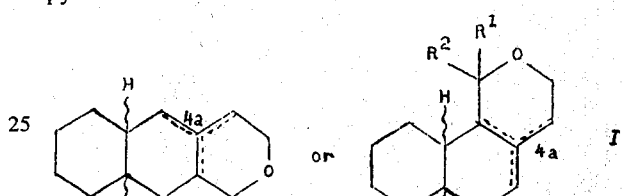

wherein $R^1$ and $R^2$ each represent lower alkyl having from 1 to 4 carbon atoms and the dotted lines indicate an optional double bond emanating from the carbon atom in the 4a position, and mixtures thereof.

2. An odoriferous composition according to claim 1, in the form of a perfume or perfume concentrate.

3. An odoriferous composition according to claim 1, in the form of a composition of the group of toilet waters, cosmetics, soaps and washing liquids.

4. An odoriferous composition according to claim 1, wherein $R^1$ and $R^2$ represent methyl.

5. An odoriferous composition according to claim 1, in which said naphthopyran is 3,5,5a,6,7,8,9,9a,10,-10a-decahydro-1,1-dimethyl-1H-naphtho[2,3-c]pyran of formula:

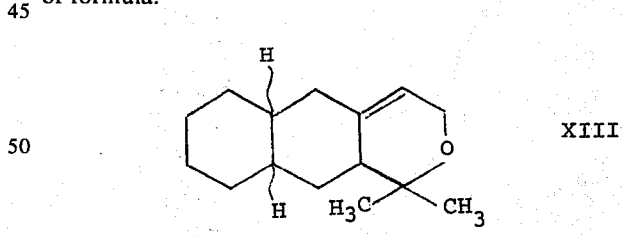

XIII

6. An odoriferous composition according to claim 1, in which said naphthopyran is 3,4,5,5a,6,7,8,9,9a,10-decahydro-1,1-dimethyl-1H-naphtho[2,3-c]pyran of formula:

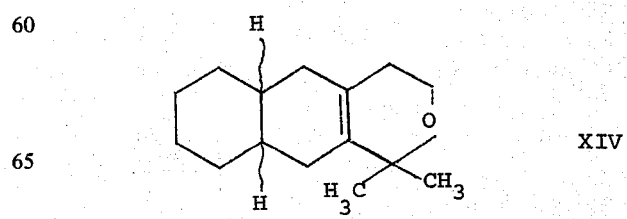

XIV

7. An odoriferous composition according to claim 1, in which said naphthopyran is 3,4,5a,6,7,8,9,9a,10,-10a-decahydro-1,1-dimethyl-1H-naphtho[2,3-c]pyran of formula:

3,951,875

7

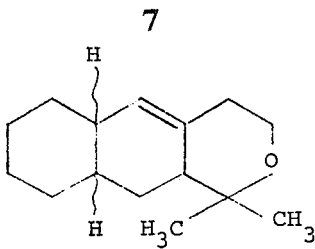

XV

8. An odoriferous composition according to claim 1, in which said naphthopyran is perhydro-1,1-dimethyl-naphtho[2,3-c]pyran of formula:

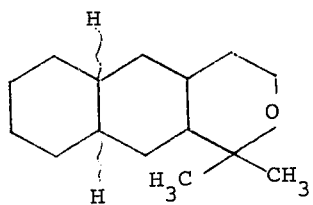

XVI

9. An odoriferous composition according to claim 1, in which said naphthopyran is 3,5,6,6a,7,8,9,10,-10a,10b-decahydro-1,1-dimethyl-1H-naphtho[1,2-c]pyran of formula:

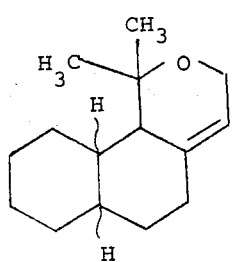

XVII

10. An odoriferous composition according to claim 1, in which said naphthopyran is 3,4,5,6,6a,7,8,9,10,-10a-decahydro-1,1-dimethyl-1H-naphtho[1,2-c]pyran of formula:

8

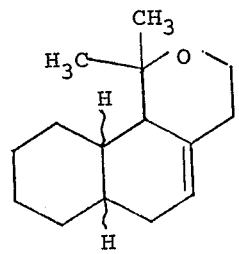

XVIII

11. An odoriferous composition according to claim 1, in which said naphthopyran is 3,4,6,6a,7,8,9,10,-10a,10b-decahydro-1,1-dimethyl-1H-naphtho[1,2-c]pyran of formula:

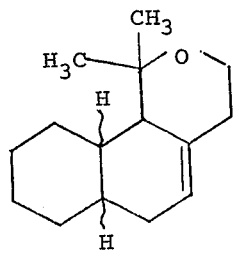

XIX

12. An odoriferous composition according to claim 1, in which said naphthopyran is perhydro-1,1-dimethyl-naphtho[1,2-c]pyran of formula:

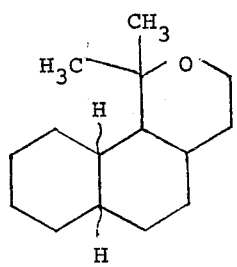

XX

* * * * *